(12) United States Patent
Nakaoka et al.

(10) Patent No.: US 8,034,039 B2
(45) Date of Patent: Oct. 11, 2011

(54) DISPOSABLE PANTS

(75) Inventors: Kenji Nakaoka, Osaka (JP); Masaru Fujioka, Tokushima (JP)

(73) Assignee: Livedo Corporation, Ehime (JP)

( * ) Notice: Subject to any disclaimer, the term of this patent is extended or adjusted under 35 U.S.C. 154(b) by 855 days.

(21) Appl. No.: 11/792,393

(22) PCT Filed: Dec. 6, 2005

(86) PCT No.: PCT/JP2005/022362
§ 371 (c)(1),
(2), (4) Date: Jun. 6, 2007

(87) PCT Pub. No.: WO2006/062090
PCT Pub. Date: Jun. 15, 2006

(65) Prior Publication Data
US 2008/0021425 A1 Jan. 24, 2008

(30) Foreign Application Priority Data
Dec. 7, 2004 (JP) .................................. 2004-353635

(51) Int. Cl.
*A61F 13/15* (2006.01)
*A61F 13/20* (2006.01)
(52) U.S. Cl. ....................................................... 604/386
(58) Field of Classification Search ............. 604/385.11, 604/393–395, 398, 402
See application file for complete search history.

(56) References Cited

U.S. PATENT DOCUMENTS

| 6,991,622 B2 | 1/2006 | Nakaoka et al. |
| 2003/0023219 A1 | 1/2003 | Nakaoka et al. |
| 2003/0055389 A1* | 3/2003 | Sanders et al. ................ 604/358 |
| 2004/0186451 A1 | 9/2004 | Bishop et al. |

FOREIGN PATENT DOCUMENTS
EP 1 269 957 1/2003
(Continued)

OTHER PUBLICATIONS

English translation of specification of JP 2004-329590 A to Fujioka.*
(Continued)

*Primary Examiner* — Melanie Hand
(74) *Attorney, Agent, or Firm* — Wenderoth, Lind & Ponack, L.L.P.

(57) ABSTRACT

Disposable pants allow a crotch section and a front abdominal section to be bonded securely while ensuring the stretchability of the front abdominal section in a pants structure in which the crotch section and front abdominal section formed as separate members are bonded. The disposable pants have functions of both pants and a diaper, and a left front abdominal part and a right front abdominal part can be developed to the left and right by breaking left and right breaking parts. The left front abdominal part and right front abdominal part are provided with adhesive pieces to be attached/detached to/from adhesive parts of a central front abdominal part. A crotch section on which an absorber is provided is connected to the central front abdominal part using sheet members so as not to interfere with stretchability of the central front abdominal part resulting from an elastic member.

17 Claims, 10 Drawing Sheets

FOREIGN PATENT DOCUMENTS

| | | |
|---|---|---|
| JP | 2-6031 | 1/1990 |
| JP | 5-9530 | 2/1993 |
| JP | 5-317356 | 12/1993 |
| JP | 6-90979 | 4/1994 |
| JP | 2002-204811 | 7/2002 |
| JP | 2004-329590 | 11/2004 |
| WO | 00/13633 | 3/2000 |
| WO | 01/58401 | 8/2001 |
| WO | 03/024682 | 3/2003 |

OTHER PUBLICATIONS

Supplementary European Search Report issued Aug. 6, 2009 in European Patent Application No. 05 81 4566.

Japanese Office Action, with partial English translation, issued Jul. 13, 2010 in connection with corresponding Japanese Application No. 2004-353635.

CD-ROM of the specification and drawings annexed to the request of Japanese Utility Model Application No. 63775/1991 (Laid-open No. 9530/1993), (Shiseido Co., Ltd.), Feb. 9, 1993.

Microfilm of the specification and drawings annexed to the request of Japanese Utility Model Application No. 84545/1988 (Laid-open No. 6031/1990), (Oji Paper Co., Ltd.), Jan. 16, 1990.

Chinese Office Action (with English translation) issued on May 25, 2011 in counterpart Chinese Application No. 201010107397.6.

Japanese Office Action, with partial English translation, issued Oct. 19, 2010 in connection with corresponding Japanese Application No. 2004-353635.

\* cited by examiner

DISPOSABLE PANTS

TECHNICAL FIELD

The present invention relates to disposable pants used as pants and a diaper.

BACKGROUND ART

As conventional disposable pants of this type, there is a technique described in Japanese Patent Application Laid-Open No. 5-317356. The pants described in this gazette are provided with breaking lines on both left and right sides of a front section to allow the front section to be separated at the breaking lines as well as adhesive pieces bonded to bonding parts on the left and right sides of the front section and a rear section. When the front section is separated at the breaking lines, the front section and rear section are fastened by the left and right adhesive pieces. Besides, an elastic stretchable member is provided around the hips of the front abdominal section.

The pants disclosed in this gazette, provided with an elastic stretchable member around the hips of the front abdominal section, have a structure in which sections including the front abdominal section, crotch section and rear section are formed integrally, which is different in fundamental structure from the disposable pants according to the present invention in which the crotch section and front abdominal section are formed as separate members and are then bonded.

That is, the structure in which the front abdominal section and crotch section are formed as separate members as in the present invention presents a great problem of how to bond the crotch section having an absorber to the front abdominal section while ensuring the contractibility of the front abdominal section. However, such a problem does not arise in the disposable pants described in the above gazette having a structure in which the front abdominal section and crotch section are integral.

DISCLOSURE OF INVENTION

The present invention has an object to provide disposable pants capable of solving the aforementioned problem and allowing a crotch section and a front abdominal section to be bonded securely while ensuring the stretchability of the front abdominal section in a pants structure in which the crotch section and front abdominal section are formed as separate members and bonded together.

In a first aspect of the present invention, the disposable pants comprise: a front abdominal section and a rear section joined almost annularly; a crotch section provided to be joined between the front abdominal section and the rear section; an absorber provided on the crotch section; left and right breaking parts provided on both left and right sides of portions in the front abdominal section to which a front side part of the crotch section is bonded, for breaking the front abdominal section; left and right adhesive pieces connected to portions in the front abdominal section on laterally outward sides from the left and right breaking parts; adhesive parts provided between the left and right breaking parts on an exterior side of the front abdominal section to/from which the left and right adhesive pieces are attached/detached; an elastic stretchable member provided in a central area in the front abdominal section positioned between the left and right breaking parts; and sheet members having one side edge bonded to the central area of the front abdominal section and the other side edge bonded to the front side part of the crotch section for connecting the front abdominal section and the crotch section.

In a second aspect of the present invention, the disposable pants comprise: a front abdominal section and a rear section joined almost annularly; a crotch section provided to be joined between the front abdominal section and the rear section; an absorber provided on the crotch section; left and right breaking parts provided on both left and right sides of portions in the front abdominal section to which a front side part of the crotch section is bonded, for breaking the front abdominal section; left and right adhesive pieces connected to portions in the front abdominal section on laterally outward sides from the left and right breaking parts; adhesive parts provided between the left and right breaking parts on an exterior side of the front abdominal section to/from which the left and right adhesive pieces are attached/detached; an elastic stretchable member provided in a central area in the front abdominal section positioned between the left and right breaking parts; and a plurality of connection parts provided at a predetermined distance in the lateral direction on a surface of the front side part of the crotch section that faces the central area of the front abdominal section, for connecting the front side part of the crotch section and the central area.

In a third aspect of the present invention, the disposable pants comprise: a front abdominal section and a rear section joined almost annularly; a crotch section provided to be joined between the front abdominal section and the rear section; an absorber provided on the crotch section; left and right breaking parts provided on both left and right sides of portions in the front abdominal section to which a front side part of the crotch section is bonded, for breaking the front abdominal section; left and right adhesive pieces connected to portions in the front abdominal section on laterally outward sides from the left and right breaking parts; adhesive parts provided between the left and right breaking parts on an exterior side of the front abdominal section to/from which the left and right adhesive pieces are attached/detached; and a first elastic stretchable member provided partially in an upper portion in the central area positioned between the left and right breaking parts of the front abdominal section, wherein a portion of the front side part of the crotch section that faces the central area is bonded to the central area from a skin-facing side such that the absorber is arranged below a region where the first elastic stretchable member is provided in the central area so as not to overlap the region.

In a fourth aspect of the present invention, in the disposable pants according to the third aspect, a second elastic stretchable member is provided in a portion positioned above an edge of the absorber in the front side part of the crotch section.

In a fifth aspect of the present invention, in the disposable pants according to the fourth aspect, the first elastic stretchable member is provided in a region on the laterally inward side from left and right edges of the central area by a first predetermined dimension, and the second elastic stretchable member is provided in a region on the laterally inward side from left and right edges of the front side part by a second predetermined dimension.

According to the first aspect, the crotch section is connected to the central area of the front abdominal section using the sheet members, which allows the central area of the front abdominal section to freely stretch and contract by extra length of the sheet members, without being affected substantially by the crotch section. As a result, connection between the crotch section and front abdominal section can be made securely while ensuring the stretchability of the central area of the front abdominal section resulting from the elastic stretchable members.

According to the second aspect, since the plurality of connection parts provided at a distance in the lateral direction connect the front side part of the crotch section and central area of the front abdominal section, a portion of the crotch section positioned between the connection parts that is not connected to the front abdominal section can be softly deformed in accordance with stretch and contraction of the central area of the front abdominal section. This can reduce the influence of the crotch section upon stretch and contraction of the central area of the front abdominal section. As a result, connection between the crotch section and front abdominal section can be made securely while ensuring the stretchability of the central area of the front abdominal section resulting from the elastic members.

According to the third aspect, the front side part of the crotch section is bonded to the central area of the front abdominal section with the absorber displaced downwardly from the region where the first elastic stretchable member is provided in the front abdominal section. This can prevent the stretchability of the portion of the central area, where the first elastic stretchable member is provided, from being interfered with by the absorber of the crotch section having poor stretchability, which allows the crotch section to be bonded securely to the front abdominal section while ensuring the stretchability of the central area resulting from the first elastic stretchable member.

Further, since the absorber is displaced downwardly from the region where the first elastic stretchable member is provided, the stretchability of the central area resulting from the first elastic stretchable member can be maintained even when bonding by an adhesive or the like is made substantially entirely on the surface of the crotch section opposed to the central area of the front abdominal section.

According to the fourth aspect, by providing the second elastic stretchable member in the portion positioned above the edge of the absorber in the aforementioned front side part of the crotch section, the stretchability of the central area of the front abdominal section can be maintained or increased.

According to the fifth aspect, since the left and right edges in the upper portions of the central area of the front abdominal section and front side part of the crotch section are not provided with any elastic stretchable member and do not contract, a caretaker can easily hold that portion. As a result, for example, operations in which a caretaker extends the elastic stretchable members on the central area and front side part of the crotch section holding the left and right edges in the upper portions of the central area of the front abdominal section and front side part of the crotch section to fit the wearer's skin, etc. can be easily carried out.

These and other objects, features, aspects and advantages of the present invention will become more apparent from the following detailed description and accompanying drawings.

DETAILED DESCRIPTION OF THE INVENTION

First Embodiment

[General Description]

Figure 1:
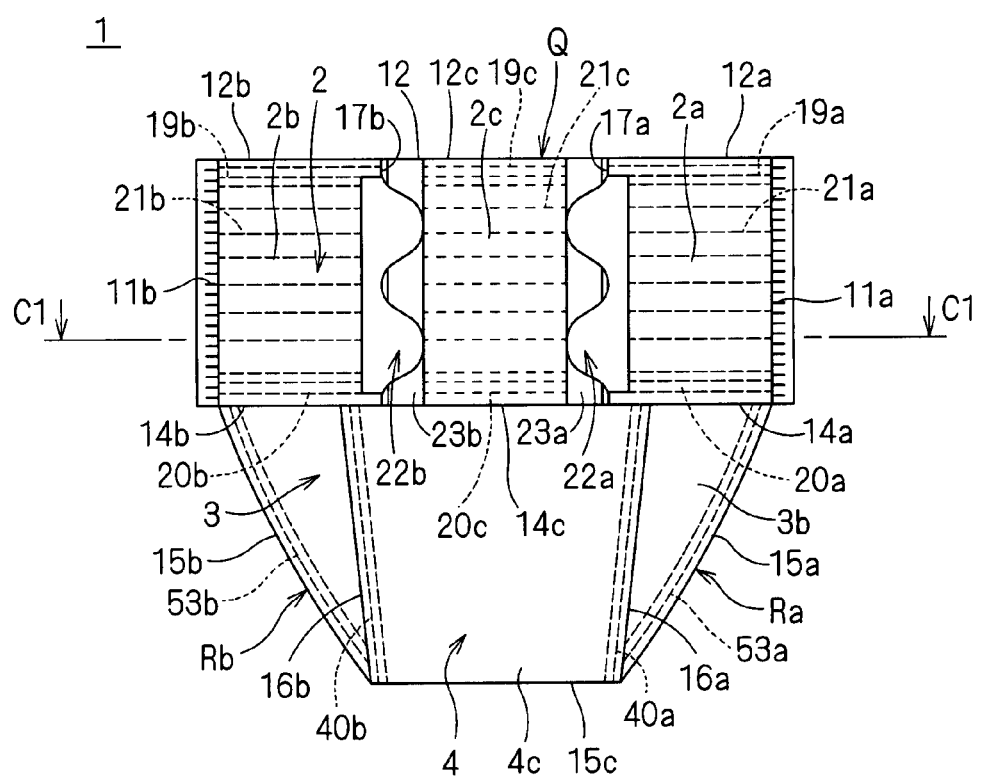
FIG. 1 is a front view of disposable pants according to a first embodiment of the present invention.

With reference to FIGS. 1 to 4, disposable pants 1 according to a first embodiment of the present invention will be described. The disposable pants 1 are, as shown in FIGS. 1 to 4, configured to comprise a front abdominal section 2 and a rear section 3 joined almost annularly and a crotch section 4 provided to be joined between the front abdominal section 2 and rear section 3, and are usable as both pants and a diaper. In the description of the disposable pants 1, the left and right shall indicate the left hand side and right hand side as viewed from a wearer.

The front abdominal section 2 and rear section 3 refer to portions of the disposable pants 1 that mainly face the front abdominal area and back of a wearer. Left and right edges of the front abdominal section 2 and left and right edges of the rear section 3 are bonded to each other, and the front abdominal section 2 and rear section 3 are thereby joined almost annularly. Accordingly, a left side bonding part 11a and a right side bonding part 11b for bonding the left and right edges of the front abdominal section 2 and left and right edges of the rear section 3 are formed on left and right edges of the disposable pants 1. Bonding at these side bonding parts 11a and 11b is created either by bonding with an adhesive such as a hot melt adhesive or ultrasonic welding (or heating welding), or by both of them in combination.

The crotch section 4 indicates a portion of the disposable pants 1 that mainly faces the crotch of a wearer, having a front crotch part 4a and a rear crotch part 4b joined to the front abdominal section 2 and rear section 3, respectively. In this embodiment, the front crotch part (front side part) 4a and rear crotch part 4b of the crotch section 4 are bonded to the front abdominal section 2 and rear section 3 by an adhesive such as a hot melt adhesive. As a variation, the crotch section 4 may be formed integrally by a member connected to the rear section 3.

A waist opening Q is formed by upper edges 12 and 13 of the front abdominal section 2 and rear section 3 joined almost annularly as described. A left leg opening Ra is formed by a lower edge 14a of a left front abdominal part 2a of the front abdominal section 2, a sloped edge 15a on the left lower side of the rear section 3 and a left edge 16a of the crotch section 4. A right leg opening Rb is formed by a lower edge 14b of a right front abdominal part 2b of the front abdominal section 2, a sloped edge 15b on the right lower side of the rear section 3 and a right edge 16b of the crotch section 4.

[Front Abdominal Section]

Figure 2:
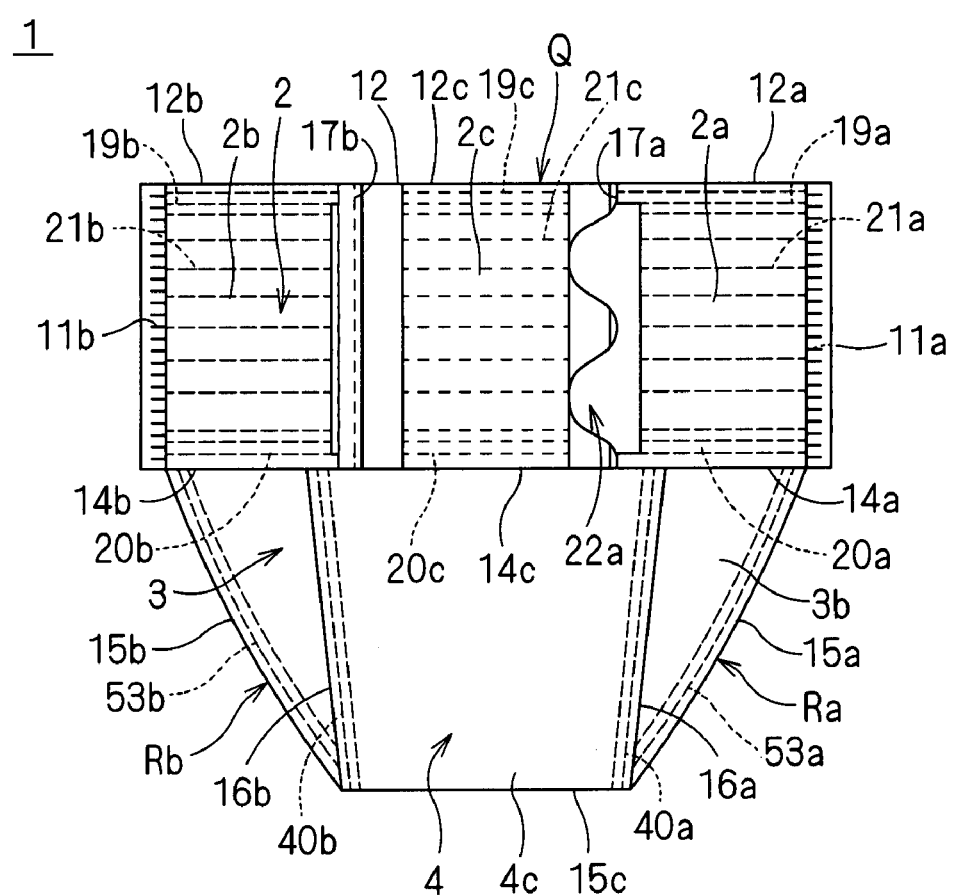
FIG. 2 is a diagram showing a broken right adhesive part of the disposable pants shown in FIG. 1.
Figure 3:
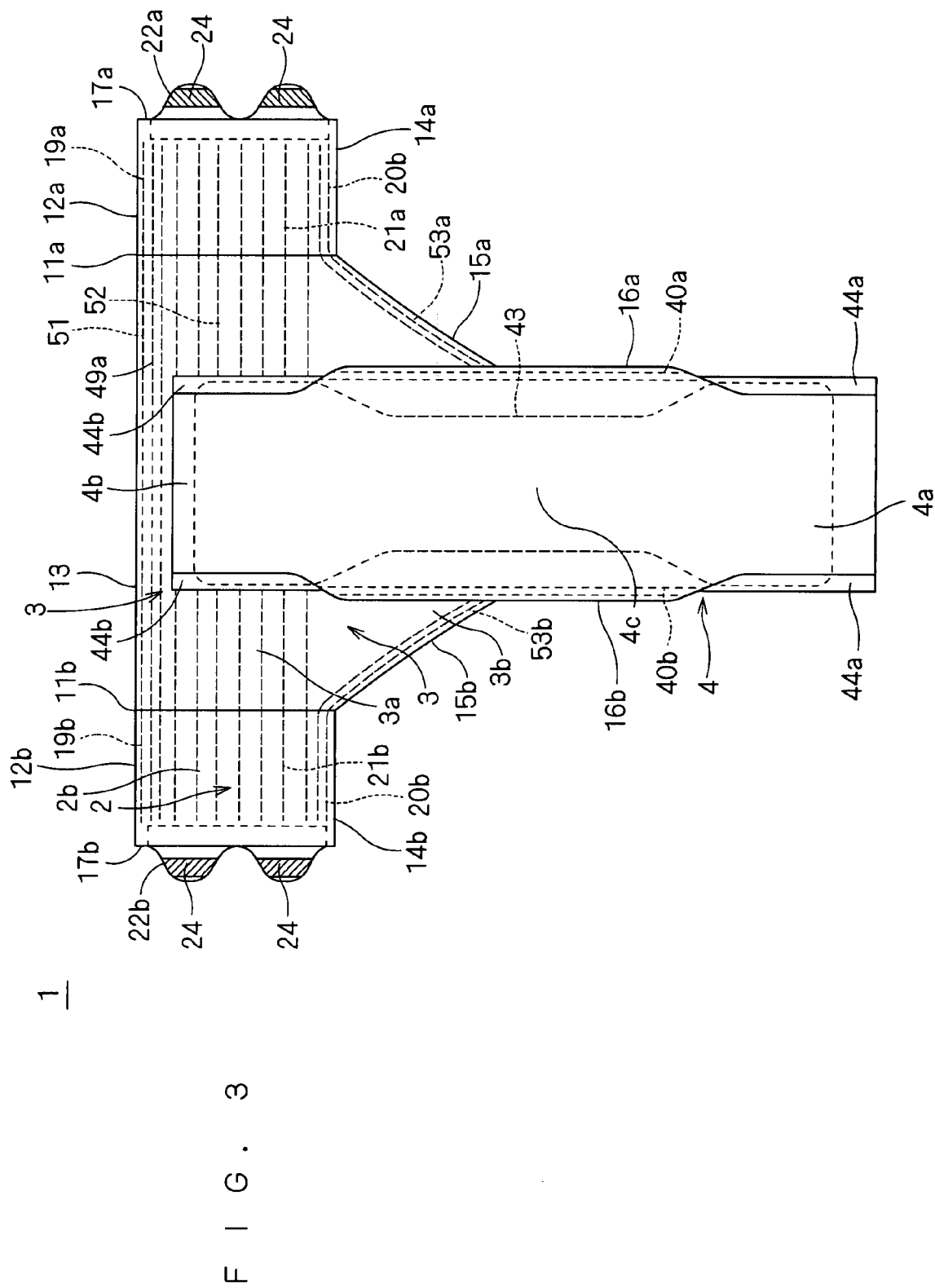
FIG. 3 is a diagram showing the state in which left and right breaking parts of the disposable pants shown in FIG. 1 are broken to develop a crotch section.

In the state extended as shown in FIG. 1, the front abdominal section 2 is of almost laterally-long rectangular shape in plan view as an overall configuration, and includes the left front abdominal part 2a, right front abdominal part 2b and a central front abdominal part 2c positioned midway between them. The central front abdominal part 2c corresponds to a central area of the present invention. A left breaking part 17a extending vertically through the front abdominal section 2 is formed between the left front abdominal part 2a and central front abdominal part 2c, and a right breaking part 17b extending vertically through the front abdominal section 2 is formed between the right front abdominal part 2b and central front abdominal part 2c. The breaking parts 17a and 17b are formed by perforations or the like, as shown in FIG. 2, and by breaking these breaking parts 17a and 17b, the front abdominal section 2 can be separated at the breaking parts 17a and 17b to be developed, as shown in FIG. 3. Here, the breaking parts 17a and 17b may be formed linearly as shown in FIG. 2, or may be formed as curved lines according to necessity.

Waist elastic members 19a, 19b and 19c are attached in a laterally stretched state to the upper edges 12a, 12b and 12c of the left front abdominal part 2a, right front abdominal part 2b and central front abdominal part 2c. Leg elastic members 20a, 20b and a front abdominal lower portion elastic member 20c are attached in a laterally stretched state to the lower edges 14a, 14b and 14c of the left front abdominal part 2a, right front abdominal part 2b and central front abdominal part 2c. Body elastic members 21a, 21b and 21c are attached in a laterally stretched state to areas between the upper edges 12a, 12b and 12c and the lower edges 14a, 14b and 14c of the left front abdominal part 2a, right front abdominal part 2b, and central front abdominal part 2c. Of these, elastic members 19c, 20c and 21c correspond to elastic stretchable members provided in the central area of the front abdominal section 2 according to the present invention.

Contraction and stretch of these elastic members 19a to 19c, 20a to 20c and 21a to 21c allows the front abdominal section 2 to fit snugly about the wearer's abdominal area.

Figure 4:
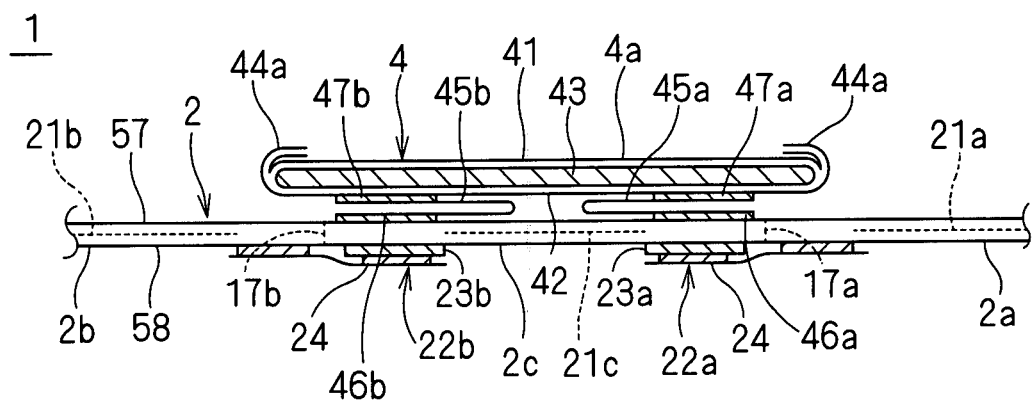
FIG. 4 is a partial sectional view along a line C1-C1 of the disposable pants shown in FIG. 1.

Such front abdominal section 2 is formed by sandwiching the elastic members 19a to 19c, 20a to 20c and 21a to 21c between an interior-layer sheet 57 on the skin-facing side and an exterior-layer sheet 58 on the exterior side, as shown in FIG. 4.

Here, in the manufacturing steps of the front abdominal section 2, these elastic members 19a to 19c, 20a to 20c and 21a to 21c are arranged continuously in the longitudinal direction (lateral direction when put on) of the front abdominal section 2, and thereafter, portions positioned around the breaking parts 17a and 17b (more specifically, portions corresponding to bonding parts of adhesive pieces 22a, 22b and portions where adhesive parts 23a, 23b are provided) are subjected to a weakening process. The weakening process is a process of partially cutting the elastic members 19a to 19c, 20a to 20c and 21a to 21c or weakening the contractile force, or the like, to thereby bring about a no-tension state.

An almost sheet-like left adhesive piece 22a and a right adhesive piece 22b are bonded to the edges of the left front abdominal part 2a and right front abdominal part 2b on the exterior side and on the side of the central front abdominal part 2c with an adhesive such as a hot melt adhesive. These adhesive pieces 22a and 22b are used for securing the pants 1 when breaking the breaking parts 17a and 17b, and are provided to straddle the left and right breaking parts 17a and 17b on the exterior side of the front abdominal section 2. Adhesive parts 23a and 23b to which the adhesive pieces 22a and 22b are to be attached are respectively provided on both side edges on the exterior side of the central front abdominal part 2c.

Adhesive parts 24 are respectively provided on the surface (skin-facing side) of the adhesive pieces 22a and 22b that can be opposed to the adhesive parts 23a and 23b. These adhesive parts 24 detachably adhere to the adhesive parts 23a and 23b provided on the central front abdominal part 2c.

Specific examples of the adhesive parts 23a and 23b may include a loop member having a nonwoven fabric, a woven fabric, a knitted material or the like with a fine loop structure being densely formed on its surface, and specific examples of the adhesive parts 24 may include a hook member with a fine hook structure in freely detachable engagement with the loop member being densely formed on its surface. Another specific example of the adhesive parts 23a and 23b may include a plastic film or the like, which is surface-treated by using PEELOIL, for example, so as to have repetitive removability from an adhesive, and another specific example of the adhesive parts 24 may include a reusable adhesive, and the like. In the above-described two specific examples of these adhesive parts 23a, 23b and those of the adhesive parts 24, the structure on the adhesive parts 23a, 23b side and the structure on the adhesive parts 24 side may be replaced with each other.

With such structure, when peeling the left and right adhesive pieces 22a and 22b from the adhesive parts 23a and 23b and pulling them outwardly in the lateral direction, the breaking parts 17a and 17b are broken, so that the left and right front abdominal parts 2a and 2b are developed to the both left and right sides integrally with the adhesive pieces 22a and 22b, as shown in FIG. 3.

In this manner, the disposable pants 1, as shown in FIG. 1, function as pants in the state at product shipping before breaking the breaking parts 17a and 17b, and are easily raised/lowered similarly to typical disposable pants having no opening/closing means such as the adhesive pieces 22a and 22b, etc.

Further, in the case where the disposable pants 1 are worn as pants and when an absorber 43 to be described later absorbs and contains bodily wastes, the adhesive pieces 22a and 22b are peeled from the adhesive parts 23a and 23b to break the breaking parts 17a and 17b and develop, so that the pants 1 can easily be removed from the wearer. In this case, the pants 1 can be removed without taking off the wearer's garments.

Further, after peeling a temporarily fixing parts of the adhesive pieces 22a and 22b to break the breaking parts 17a, 17b and develop the front abdominal section 2 to see how the inside of the pants 1 gets soiled, the adhesive pieces 22a and 22b may be engaged with the adhesive parts 23a and 23b, to thereby return the pants 1 to its original state as pants. Further, when the pants 1 and an optional pad such as a urine pad are used in combination, the adhesive pieces 22a and 22b can be attached/detached to facilitate replacing such optional pad, and the like.

Further, the pants 1 may be used as a typical disposable diaper applying the pants as developed as shown in FIG. 3 before putting them on, around the wearer's hips, so that the pants 1 can be used as a typical disposable diaper. In this case, the pants 1 can be put on and removed without taking off wearer's garments.

[Crotch Section]

In the developed state extended as shown in FIG. 3, the crotch section 4 has an almost strip shape extending in the front-to-rear direction when developed, as an overall configuration, and includes the front crotch part 4a, rear crotch part 4b and central crotch part 4c positioned midway between them, and is applied to the crotch of a wearer mainly setting the central crotch part 4c at the center. The front crotch part 4a is bonded to the central front abdominal part 2c in the state overlapping the interior side of the central front abdominal part 2c, as shown in FIG. 3. The rear crotch part 4b is bonded and fixed to the rear section 3 in the state overlapping the interior side of the rear section 3, as shown in FIG. 3. Leg elastic members 40a and 40b are attached to left edge 16a and right edge 16b of such crotch section 4 in a stretched state in the direction that the edges 16a and 16b extend.

As shown in FIG. 4, the crotch section 4 is formed by sandwiching the absorber 43 between a liquid-permeable top sheet 41 and a liquid-impermeable backsheet 42. The absorber 43 has a predetermined width and extends in the front-to-rear direction in the form of strip with the central crotch part 4c set at the center. In the front crotch part 4a and rear crotch part 4b of the crotch section 4, portions 44a and 44b of the top sheet 41 and backsheet 42 that extend off the absorber 43 to the left and right are bonded and fixed in the state folded back to the skin-facing side. The action of this folded structure of the both front and rear edges to the skin-facing side and the contractile force of the leg elastic members 40a and 40b causes the both left and right side edges of the crotch section 4 to be raised to the skin-facing side so as to fit the wearer's legs. The leg elastic members 40a and 40b are bonded and fixed in the state sandwiched between the top sheet 41 and backsheet 42.

For instance, the top sheet 41 is made of a liquid-permeable nonwoven fabric or the like, and the backsheet 42 is made of a water-repellant nonwoven fabric or the like. The absorber 43 is formed, for example, by covering a mass of a hydrophilic fiber assembly layer such as crushed pulp fibers or cellulose fibers mixed with a particulate gelling agent, with a covering sheet such as a sheet of paper like tissue paper, a liquid-permeable nonwoven sheet or the like, and is formed in a predetermined shape.

As a variation of structure of the crotch section 4, the absorber 43 may be adhered to the skin-facing side of the sheet 42, rather than sandwiching the absorber 43 between the sheets 41 and 42, and the sheet 41 may be omitted. Alternatively, the absorber 43 with sheets bonded to its front and rear edges may be used as the crotch section 4, or a large absorber 43 may be used as the crotch section 4 and the sheets 41 and 42 may be omitted.

[Connection Structure Between Crotch Section and Front Abdominal Section]

Connection between the front crotch part 4a and central front abdominal part 2c is made using a plurality of (e.g., two) sheet members 45a and 45b serving as connection parts. The sheet members 45a and 45b are made of a material that softly deforms, and have a vertical dimension almost equal or slightly smaller than the vertical dimension of the central front abdominal part 2c. Then, in the state where the sheet members 45a and 45b are slackened almost in the form of U as viewed from above the pants 1, their one side edges 46a and 46b are bonded to the central front abdominal part 2c by an adhesive (e.g., hot melt adhesive) or the like, and the other side edges 47a and 47b are bonded to the front crotch part 4a by an adhesive (e.g., hot melt adhesive) or the like. Such sheet members 45a and 45b are provided symmetrically at a predetermined distance in the lateral direction.

This allows the central front abdominal part 2c to freely stretch and contract by the elastic members 19c, 20c and 21c by the extra length of the sheet members 45a and 45b, without being affected substantially by the front crotch part 4a.

<Rear Section>

As shown in FIG. 3, the rear section 3 has such a form that, when developed, left and right lower side corners of an almost rectangular shape are cut almost diagonally, and are applied to an area from the waist to hips on the wearer's back. For this purpose, this rear section 3 includes the waist zone 3a in the form of almost laterally long strip in plan view mainly positioned on the waist on the wearer's back and a hip zone 3b of almost trapezoidal form in plan view joined downwardly to the waist zone 3a and mainly positioned on the wearer's hips. A waist elastic member 51 is attached in a laterally stretched state to the upper edge 13 of the waist zone 3a, and a body elastic member 52 is attached in a laterally stretched state to the other area of the waist zone 3a that does not overlap the absorber 43 of the crotch section 4.

Here, in the manufacturing steps of the rear section 3, the body elastic member 52 is continuously provided on a portion corresponding to the waist zone 3a in the lateral direction of the rear section 3, and then, a portion overlapping the crotch section 4 (or absorber 43) is to be subjected to the weakening process.

A leg elastic member 53a is attached to the sloped edge 15a on the left lower side of the rear section 3 in a stretched state along the edge 15a, and a leg elastic member 53b is attached to the sloped edge 15b on the right lower side of the rear section 3 in a stretched state along the edge 15b. Contraction and stretch of these elastic members 51, 52, 53a and 53b allows the rear section 3 to easily fit the wearer's back and hips.

Here, the leg elastic members 53a and 53b are continuously attached to the hip zone 3b along the left and right sloped edges 15a, 15b and lower edge 15c of the hip zone 3b, and then, at least portions overlapping the absorber 43 of the crotch section 4 are to be subjected to the weakening process.

[Other Structure and Material for Respective Parts, Etc.]

For the elastic members 19a to 19c, 20a to 20c, 21a to 21c, 40a, 40b, 46, 53a and 53b, an elastic stretchable material (polyurethane thread, polyurethane film, natural rubber, etc.) typically used for disposable pants is employed, and is attached to a specified position of the pants 1 in a stretched state by adhering means such as a hot melt adhesive, heating welding, ultrasonic welding or the like.

[Summary]

As described, in the disposable pants 1 according to the present invention, the front crotch part 4a is connected to the central front abdominal part 2c using the sheet members 45a and 45b, which allows the central front abdominal part 2c to freely stretch and contract by the extra length of the sheet members 45a and 45b, without being affected substantially by the crotch section 4. As a result, connection between the crotch section 4 and front abdominal section 2 can be made securely while ensuring the stretchability of the central front abdominal part 2c resulting from the elastic members 19c, 20c and 21c.

[Variation]

Figure 5:
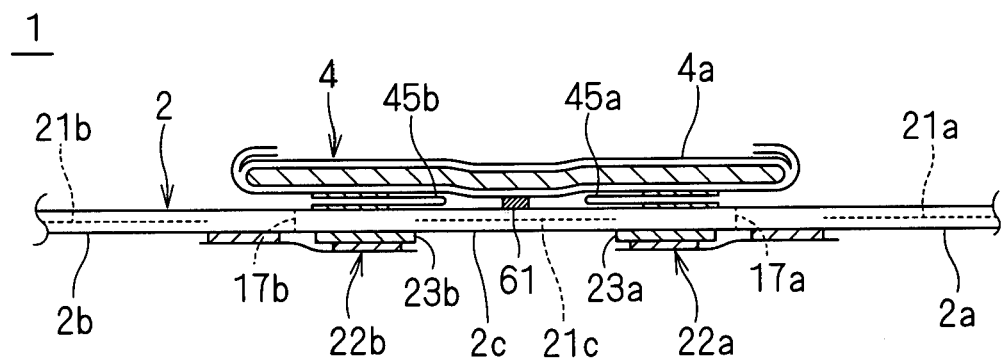
FIG. 5 is a sectional view showing a first variation of the structure of FIG. 4.
Figure 6:
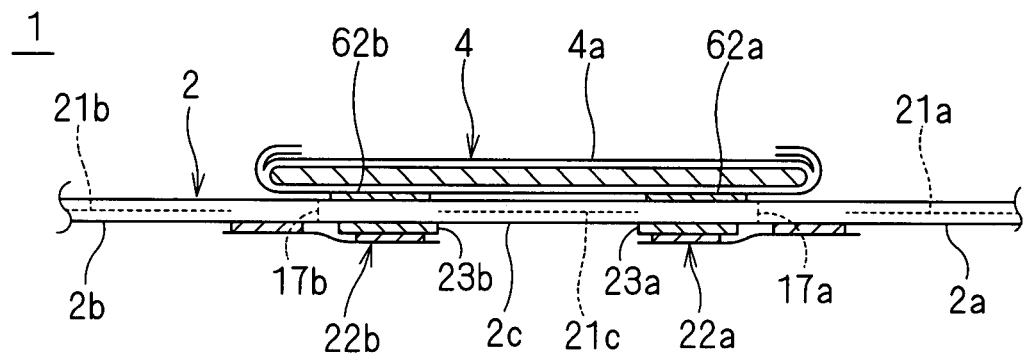
FIG. 6 is a sectional view showing a second variation of the structure of FIG. 4.
Figure 7:
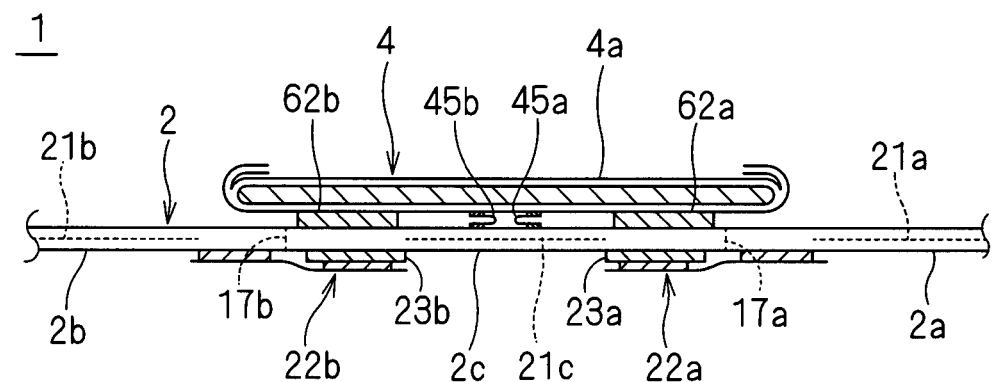
FIG. 7 is a sectional view showing a third variation of the structure of FIG. 4.

Variations of aforementioned connection structure between the crotch section 4 and front abdominal section 2 shown in FIG. 4 may include structures shown in FIGS. 5 to 7, for example.

In the first variation shown in FIG. 5, the front crotch part 4a and central front abdominal part 2c are directly connected using an adhesive (e.g., hot melt adhesive) at a vertically-long linear connection part 61 of narrow width positioned between the left and right sheet members 45a and 45b. This can prevent the crotch section 4 from being displaced to the left and right with respect to the front abdominal section 2, and achieves improvement in fixed strength of the crotch section 4.

In the second variation shown in FIG. 6, the front crotch part 4a and central front abdominal part 2c are directly connected using an adhesive (e.g., hot melt adhesive) at a plurality of (e.g., two) vertically-long linear connection parts 62a and 62b provided at a distance in the lateral direction. In the example illustrated in FIG. 6, the two vertically-long linear connection parts 62a and 62b are provided symmetrically at a distance. More specifically, the connection parts 62a and 62b are formed close to the breaking parts 17a and 17b so as to reduce the influence of the crotch section 4 upon stretch and contraction of the front abdominal section 2 as much as possible, with the maximum distance being ensured therebetween. Further, since the portions of the central front abdominal part 2c where the adhesive parts 23a and 23b are provided are not necessarily required to have stretchability, the connection parts 62a and 62b are provided on the other side surface (skin-facing side) in correspondence with the adhesive parts 23a and 23b.

With the structure shown in FIG. 6, a portion of the crotch section 4 positioned between the connection parts 62a and 62b that is not connected to the central front abdominal part 2c can be softly deformed in accordance with stretch and contraction of the central front abdominal part 2c. Accordingly, the influence of the crotch section 4 upon stretch and contraction of the front abdominal section 2 can be reduced. As a result, connection between the crotch section 4 and front abdominal section 2 can be made securely while ensuring the stretchability of the central front abdominal part 2c resulting from the elastic members 19c, 20c and 21c.

The third variation shown in FIG. 7 has a structure combining the aforementioned structure shown in FIG. 4 and the structure shown in FIG. 6. That is, using the structure shown in FIG. 6 as a basic structure, a connection structure using the sheet members 45a and 45b shown in FIG. 4 is provided in a region between the left and right connection parts 62a and 62b. This can prevent the portion of the crotch section 4 positioned between the connection parts 62a and 62b from being raised to the skin-facing side or being deformed, and achieves improvement in fixed strength of the crotch section 4.

Second Embodiment

With reference to FIGS. 8 to 13, disposable pants 71 according to a second embodiment of the present invention will be described. The disposable pants 71 have almost similar structure to the disposable pants 1 according to the aforementioned first embodiment, except the structure of securing the adhesive pieces 22a, 22b, etc., the connection structure of the crotch section 4 to the front abdominal section 2, the arrangement of elastic members, and the like. Therefore, in the structure of pants 71, parts common to the aforementioned pants 1 are indicated by the same reference numerals, and their explanations are omitted.

In the disposable pants 71 according to the present embodiment, as shown in FIGS. 8 to 13, only the waist elastic member (first elastic stretchable member) 19c is attached to the upper edge of the central front abdominal part 2c, and other elastic members 20c and 21c provided on the central front abdominal part 2c are subjected to the weakening process.

Figure 9:
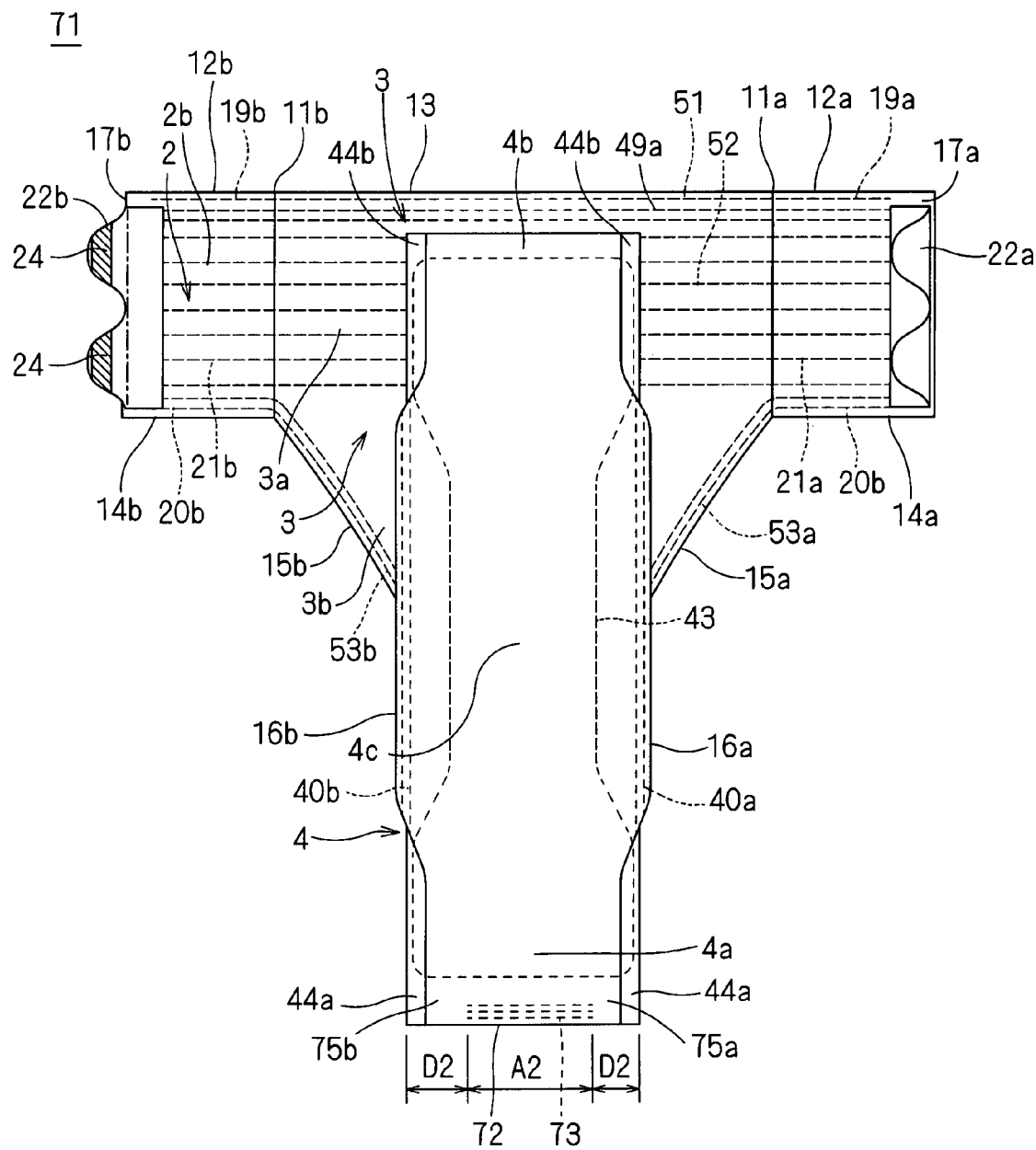
FIG. 9 is a diagram showing the state in which left and right breaking parts of the disposable pants shown in FIG. 8 are broken to develop a crotch section.
Figure 10:
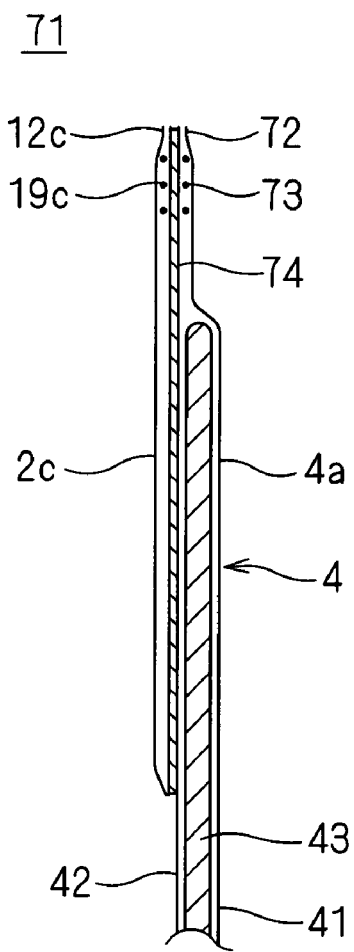
FIG. 10 is a partial sectional view along a line C2-C2 of the disposable pants shown in FIG. 8.

Further, as shown in FIGS. 9 and 10, a waist elastic member (second elastic stretchable member) 73 is also provided in a portion positioned above the upper edge of the absorber 43 in the front crotch part 4a (e.g., upper edge 72 of the front crotch part 4a). This waist elastic member 73 is attached as sandwiched between the top sheet 41 and backsheet 42 of the crotch section in a laterally stretched state.

Figure 11:
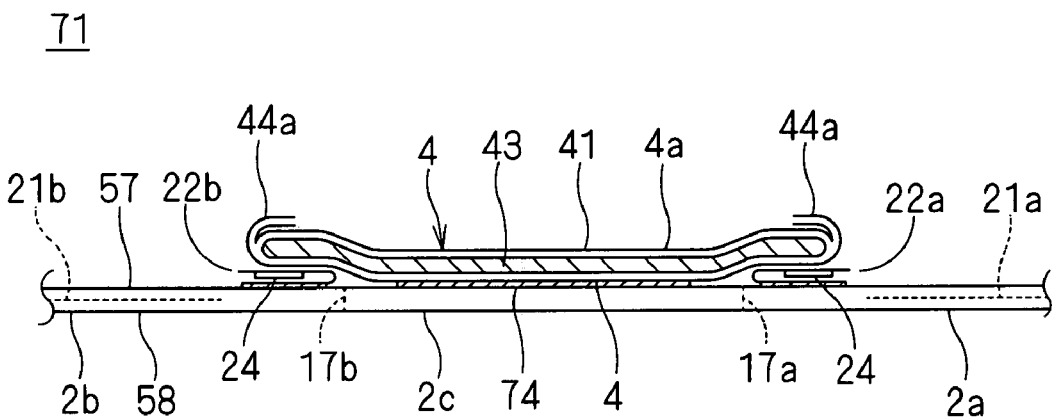
FIG. 11 is a partial sectional view along a line C3-C3 of the disposable pants shown in FIG. 8.
Figure 12:
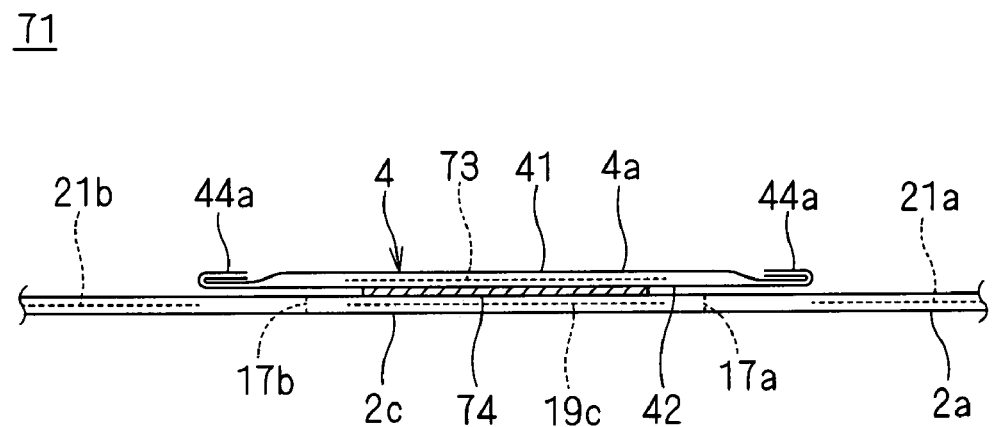
FIG. 12 is a partial sectional view along a line C4-C4 of the disposable pants shown in FIG. 8.

Then, the front crotch part 4a is bonded to the central front abdominal part 2c almost entirely on the surface opposed to the skin-facing side by an adhesive (e.g., hot melt adhesive) 74. In such bonded state, as shown in FIGS. 10 to 12, the absorber 43 of the crotch section 4 is positioned below the portion where the waist elastic member 19c of the central front abdominal part 2c is provided so as not to interfere with stretch and contraction of upper portions of the central front abdominal part 2c and front crotch part 4a resulting from the waist elastic members 19c and 73. The upper edge 72 of the front crotch part 4a is almost aligned with the upper edge 12c of the central front abdominal part 2c, and in this state, the both waist elastic members 19c and 73 are opposed to each other.

Figure 8:
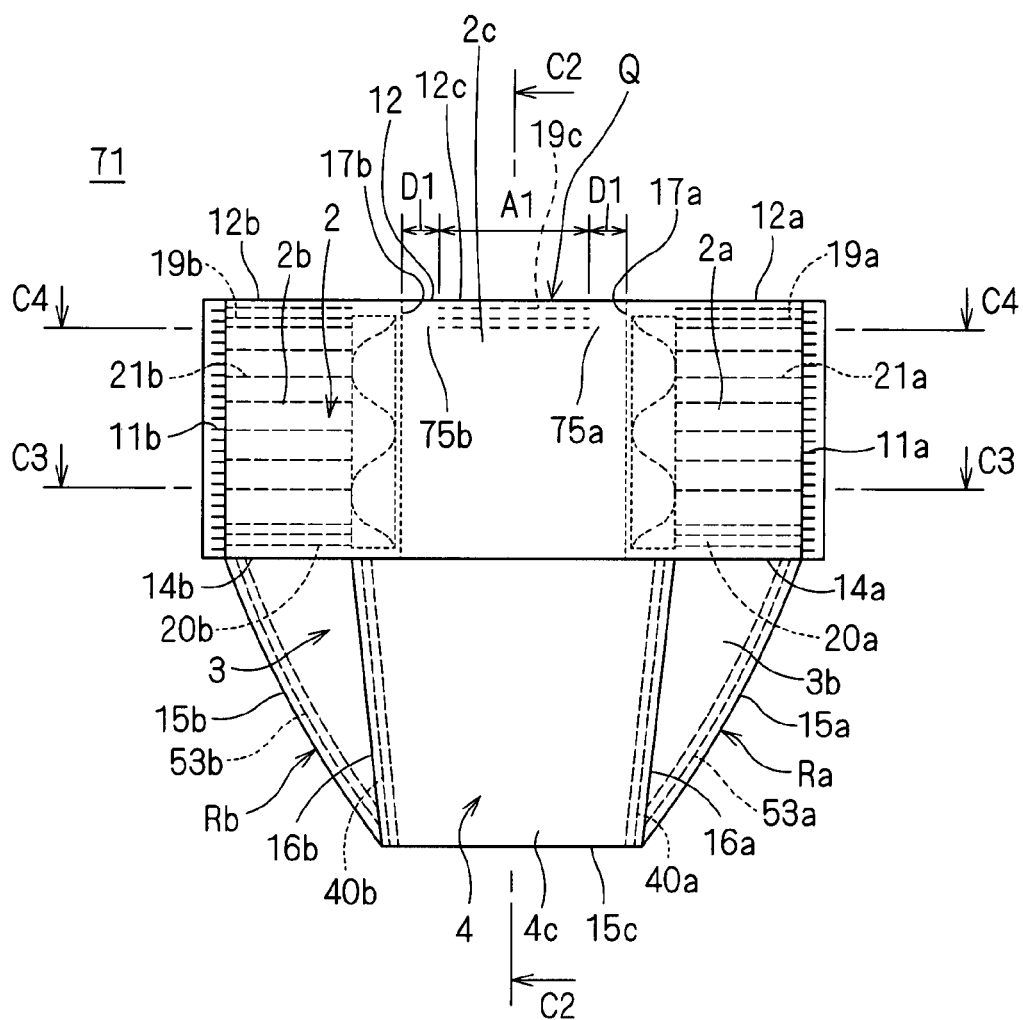
FIG. 8 is a front view of disposable pants according to a second embodiment of the present invention.

Further, the waist elastic member 19c is provided in a region A1 on the laterally inward side from the left and right edges of the central front abdominal part 2c by a first predetermined dimension D1 as shown in FIG. 8, and the waist elastic member 73 is also provided in a region A2 on the laterally inward side from the left and right edges of the front crotch part 4a by a second predetermined dimension D2 as shown in FIG. 9. The regions A1 and A2 are set almost equal in lateral width dimension. Accordingly, left and right edges 75a and 75b in the upper portions of the central front abdominal part 2c and front crotch part 4a, not provided with the elastic members 19c and 73, are intended not to contract when the breaking parts 17a and 17b are broken so that the pants 71 are developed as shown in FIG. 9.

In the present embodiment, the left and right adhesive pieces 22a and 22b are provided in the state folded to the skin-facing side of the front abdominal section 2 at the time of shipping from factory, as shown in FIGS. 8 and 11.

The exterior side surface of the central front abdominal part 2c is formed to function as an adhesive part, and the aforementioned adhesive parts 23a and 23b are omitted.

Figure 13:
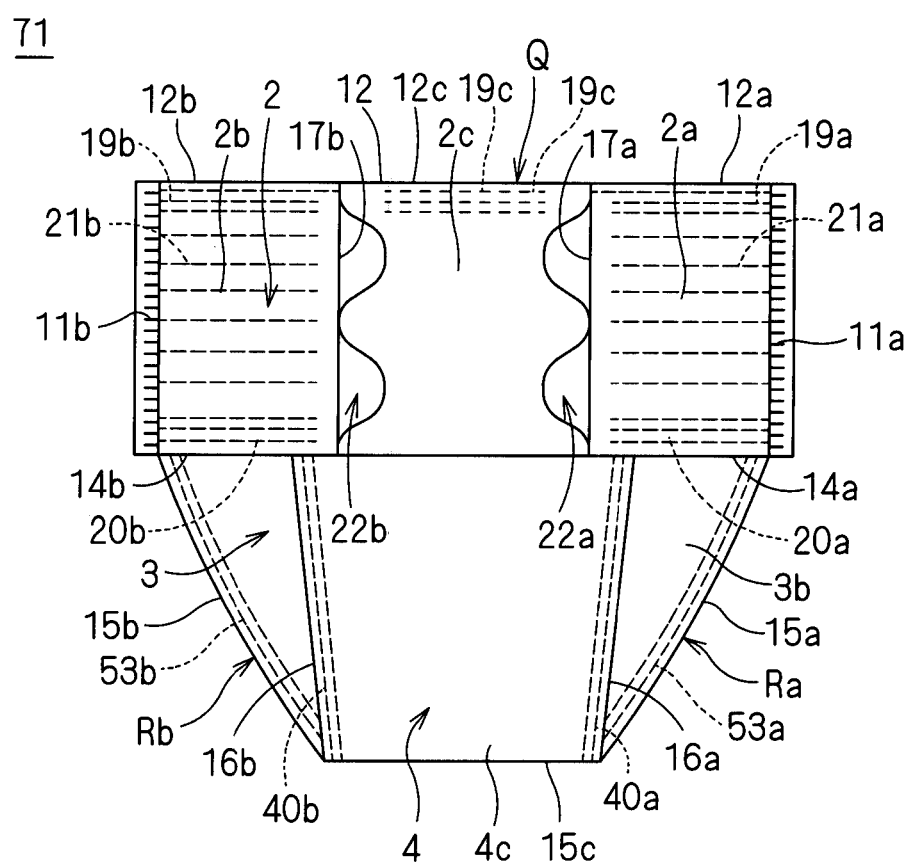
FIG. 13 is a diagram showing the state in which the disposable pants shown in FIG. 8 are used as a diaper.

In the case where the pants 71 are used as a diaper, the left and right breaking parts 17a and 17b are broken to develop the pants 71 as a diaper and to develop the folded left and right adhesive pieces 22a and 22b, as shown in FIG. 9. Then, with the pants 71 applied to the crotch of a wearer, the adhesive parts 24 of the left and right adhesive pieces 22a and 22b are attached to the exterior side surface of the central front abdominal part 2c as shown in FIG. 13. At this time, the central front abdominal part 2c and front crotch part 4a can be easily extended holding the left and right edges 75a and 75b to fit to the wearer's skin, since the left and right edges 75a and 75b in the upper portions of the central front abdominal part 2c and front crotch part 4a are formed not to contract.

As described, according to the present embodiment, the front crotch part 4a is bonded to the central front abdominal part 2c with the absorber 43 displaced downwardly from the region where the waist elastic member 19c is provided in the central front abdominal part 2c. This can prevent the stretchability of the portion of the central front abdominal part 2c provided with the elastic member 19c from being interfered with by the absorber 43 of the crotch section 4 having poor stretchability, which allows the front crotch section 4 to be securely bonded to the front abdominal section 2 while ensuring the stretchability of the central front abdominal part 2c resulting from the elastic member 19c.

Further, since the absorber 43 is displaced downwardly from the region where the elastic member 19c is provided in the central front abdominal part 2c, the stretchability of the central front abdominal part 2c resulting from the elastic member 19c can be maintained even when bonding by an adhesive is made substantially entirely on the opposed surfaces of the crotch section 4 and central front abdominal part 2c as in the present embodiment.

Further, by providing the waist elastic member 73 also in the portion located above the upper edge of the absorber 43 in the front crotch part 4a, the stretchability of the central front abdominal part 2c can be maintained or increased.

Further, since the left and right edges 75a and 75b in the upper portions of the central front abdominal part 2c and front crotch part 4a are formed not to contract, operations such as extending the central front abdominal part 2c and front crotch part 4a holding the left and right edges 75a and 75b to fit the wearer's skin, and the like can be easily carried out.

The invention claimed is:

1. Disposable pants comprising:
a front abdominal section and a rear section joined to form a waist opening;
a crotch section joined to said rear section and having a front side part connected to a central area of said front abdominal section;
an absorber provided on said crotch section;
left and right breaking parts provided on left and right sides, respectively, of said central area of said front abdominal section for breaking said front abdominal section;
a left adhesive piece connected to said front abdominal section on a laterally outward side of said left breaking part;
a right adhesive piece connected to said from abdominal section on a laterally outward side of said right breaking part;
adhesive parts provided between said left and right breaking parts on an exterior side of said front abdominal section, said left adhesive piece and said right adhesive piece being attachable to and detachable from said adhesive parts;
an elastic stretchable member provided in said central area of said front abdominal section between said left and right breaking parts; and
sheet members connecting said front abdominal section to said crotch section, each of said sheet members being sandwiched between said central area of said front abdominal section and said front side part of said crotch section and each of said sheet members having one side edge bonded to said central area of said front abdominal section and the other side edge bonded to said front side part of said crotch section in a configuration in which the sheet members are slackened in the form of a U as viewed from above,
wherein said sheet members deform to allow stretching of said elastic stretchable member, and
wherein each of said sheet members is bonded to said central area of said front abdominal section at a position between said left and right breaking parts.

2. Disposable pants comprising:
a front abdominal section and a rear section joined to form a waist opening;
a crotch section joined to said rear section and having a front side part connected to a central area of said front abdominal section;
an absorber provided on said crotch section;
left and right breaking parts provided on left and right sides, respectively, of said central area of said front abdominal section for breaking said front abdominal section;
a left adhesive piece connected to said front abdominal section on a laterally outward side of said left breaking part;
a right adhesive piece connected to said from abdominal section on a laterally outward side of said right breaking part;
adhesive parts provided between said left and right breaking parts on an exterior side of said front abdominal section, said left adhesive piece and said right adhesive piece being attachable to and detachable from said adhesive parts;
an elastic stretchable member provided in said central area of said front abdominal section between said left and right breaking parts; and
a plurality of connection parts connecting said front abdominal section to said crotch section,
wherein said connection parts are spaced apart in a lateral direction on a surface of said front side part of said crotch section,
wherein said connection parts are positioned between said left and right breaking parts on laterally outward sides of said elastic stretchable member, and said front side part of said crotch section and said abdominal section are not bonded in between said connection parts.

3. Disposable pants comprising:
a front abdominal section and a rear section joined to form a waist opening; a crotch section joined to said rear section and having a front side part connected to a central area of said front abdominal section;
an absorber provided on said crotch section;
left and right breaking parts provided on left and right sides, respectively, of said central area of said front abdominal section for breaking said front abdominal section;
a left adhesive piece connected to said front abdominal section on a laterally outward side of said left breaking part;
a right adhesive piece connected to said from abdominal section on a laterally outward side of said right breaking part;
adhesive parts provided between said left and right breaking parts on an exterior side of said front abdominal section, said left adhesive piece and said right adhesive piece being attachable to and detachable from said adhesive parts;
a first elastic stretchable member provided in an upper portion of said central area of said front abdominal section between said left and right breaking parts of said front abdominal section; and
a second elastic stretchable member provided in said front side part of said crotch section at a position adjacent to said first elastic stretchable member,
wherein a portion of said front side part of said crotch section that faces said central area of said front abdominal section is bonded to a skin-facing side of said central area of said front abdominal section,
wherein said absorber is arranged below a region where said first elastic stretchable member and said second elastic stretchable member are provided so as not to overlap the region,
wherein said first elastic stretchable member is provided in a region on the laterally inward side of left and right edges of said central area of said front abdominal section and spaced from said left and right edges of said central area of said from abdominal section by a first predetermined dimension, and
said second elastic stretchable member is provided in a region on the laterally inward side of left and right edges of said front side part of said crotch section and spaced from said left and right edges of said front side part of said crotch section by a second predetermined dimension.

4. The disposable pants of claim 1, wherein a linear connection part is provided between said sheet members, said linear connection part being connected to said central area of said front abdominal section and said front side part of said crotch section.

5. The disposable pants of claim 1, further comprising a plurality of connection parts disposed between said left and right breaking parts on laterally outward sides of said sheet members,
wherein said connection parts are sandwiched between said central area of said front abdominal section and said front side part of said crotch section, and connect said front abdominal section to said crotch section.

6. Disposable pants comprising:
a front abdominal section and a rear section joined to form a waist opening;
a crotch section joined to said rear section and having a front side part connected to a central area of said front abdominal section;
an absorber provided on said crotch section;
left and right breaking parts provided on left and right sides, respectively, of said central area of said front abdominal section for breaking said front abdominal section;
a left adhesive piece connected to said front abdominal section on a laterally outward side of said left breaking part;
a right adhesive piece connected to said from abdominal section on a laterally outward side of said right breaking part;
adhesive parts provided between said left and right breaking parts on an exterior side of said front abdominal section, said left adhesive piece and said right adhesive piece being attachable to and detachable from said adhesive parts;
an elastic stretchable member provided in said central area of said front abdominal section between said left and right breaking parts; and
sheet members connecting said front abdominal section to said crotch section, each of said sheet members being sandwiched between said central area of said front abdominal section and said front side part of said crotch section and having one side edge bonded to said central area of said front abdominal section and the other side edge bonded to said front side part of said crotch section,
wherein said sheet members deform to allow stretching of said elastic stretchable member, and
wherein a vertical dimension of each of said sheet members is substantially equal to a vertical dimension of said central area of said front abdominal section.

7. The disposable pants of claim 2, wherein each of said connection parts has a first surface attached to said central area of said front abdominal section and a second surface attached to said front side part of said crotch section.

8. The disposable pants of claim 2, further comprising sheet members disposed between said connection parts, each of said sheet members having one side edge bonded to said central area of said front abdominal section and the other side edge bonded to said front side part of said crotch section.

9. The disposable pants of claim 8,
wherein one side of each sheet member is connected to said central area of said front abdominal section and the other side of each sheet member is connected to said front side part of said crotch section.

10. The disposable pants of claim 3, wherein said absorber is arranged so as to allow stretching of said second elastic stretchable member.

11. The disposable pants of claim 3, wherein said second elastic stretchable member is opposed to said first elastic stretchable member and configured to allow said front side part of said crotch section to stretch with said central area of said front abdominal section.

12. The disposable pants of claim 1, wherein each sheet member is connected between said central area of said front abdominal section and said front side part of said crotch section in a configuration such that an extra length of the sheet member allows the central front abdominal part to stretch and contract without being substantially affected by the front crotch section.

13. The disposable pants of claim 1, wherein said elastic stretchable member includes a waist elastic member at a top edge of said central area of said front abdominal section, a lower portion elastic member at a bottom edge of said central area of said front abdominal section, and a body elastic member between said waist elastic member and said lower portion elastic member.

14. The disposable pants of claim 6, wherein a linear connection part is provided between said sheet members, said linear connection part being connected to said central area of said front abdominal section and said front side part of said crotch section.

15. The disposable pants of claim 6, further comprising a plurality of connection parts disposed between said left and right breaking parts on laterally outward sides of said sheet members,
wherein said connection parts are sandwiched between said central area of said front abdominal section and said front side part of said crotch section, and connect said front abdominal section to said crotch section.

16. The disposable pants of claim 6, wherein each sheet member is connected between said central area of said front abdominal section and said front side part of said crotch section in a configuration such that an extra length of the sheet member allows the central front abdominal part to stretch and contract without being substantially affected by the front crotch section.

17. The disposable pants of claim 6, wherein said elastic stretchable member includes a waist elastic member at a top edge of said central area of said front abdominal section, a lower portion elastic member at a bottom edge of said central area of said front abdominal section, and a body elastic member between said waist elastic member and said lower portion elastic member.

* * * * *